United States Patent [19]

McDonald et al.

[11] Patent Number: 5,438,710
[45] Date of Patent: Aug. 8, 1995

[54] THERMAL NOSE PROTECTOR AND SKI GOGGLES

[75] Inventors: Neil McDonald, Beaconsfield, Canada; Kathleen McDonald, 320, rue Penn, Beaconsfield, Québec, Canada, H9W 1B6; Sharon McDonald, Beaconsfield, Canada

[73] Assignee: Kathleen McDonald, Beaconsfield, Canada

[21] Appl. No.: 194,271

[22] Filed: Feb. 10, 1994

[51] Int. Cl.⁶ .................... A61F 9/02; A41D 13/00
[52] U.S. Cl. ........................... 2/439; 2/9; 2/13; 2/426
[58] Field of Search ........... 2/9, 13, 15, 425, 426, 2/909; 351/136; 24/306, 442

[56] References Cited

U.S. PATENT DOCUMENTS

| 3,768,100 | 10/1973 | Colman | 2/9 |
| 3,878,563 | 4/1975 | Pulju | 2/9 |
| 4,250,577 | 2/1981 | Smith | 2/9 X |
| 4,674,133 | 6/1987 | Oschner | 2/9 X |
| 4,854,015 | 8/1989 | Shaull | 24/306 X |
| 5,048,158 | 9/1991 | Koerner | 24/442 X |

FOREIGN PATENT DOCUMENTS 1274956 10/1990 Canada.
1279978 2/1991 Canada.
549256 11/1942 United Kingdom ............ 2/13

Primary Examiner—Clifford D. Crowder
Assistant Examiner—Shirra L. Jenkins
Attorney, Agent, or Firm—Pierre Lespérance; Franois Martineau

[57] ABSTRACT

A thermal nose protector for use in subfreezing climates, e.g. by an alpine skier with ski goggles. The thermal nose protector consists of a flexible shield sheet material sized to conformingly fit over the skier's nose and having at least a first and a second layer. The first layer is made from a soft, thermally insulating material for direct engagement with the skin of the skier's nose. The second layer is of the multiple-hook type for separable gripping engagement with a corresponding portion of the foam-like, peripheral, interior strip of the ski goggles. The flexible shield sheet extends beyond the tip of the skier's nose whereby a substantially open air pocket is defined by the nose-covering the shield sheet beneath the skier's nose and ahead of the skier's mouth, wherein an air breathing channel is formed coextensively of the open air pocket for promoting air breathing from the nose of the skier. The air breathing channel extends generally transversely of the direction of displacement of the skier whereby the nose of the skier is thermally protected from incoming wind.

3 Claims, 2 Drawing Sheets

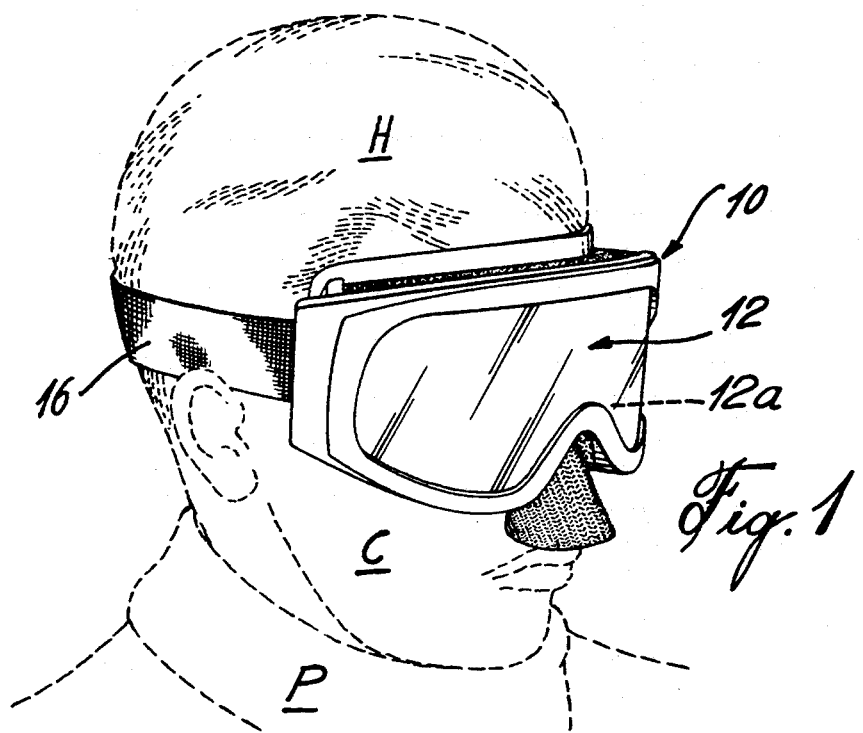
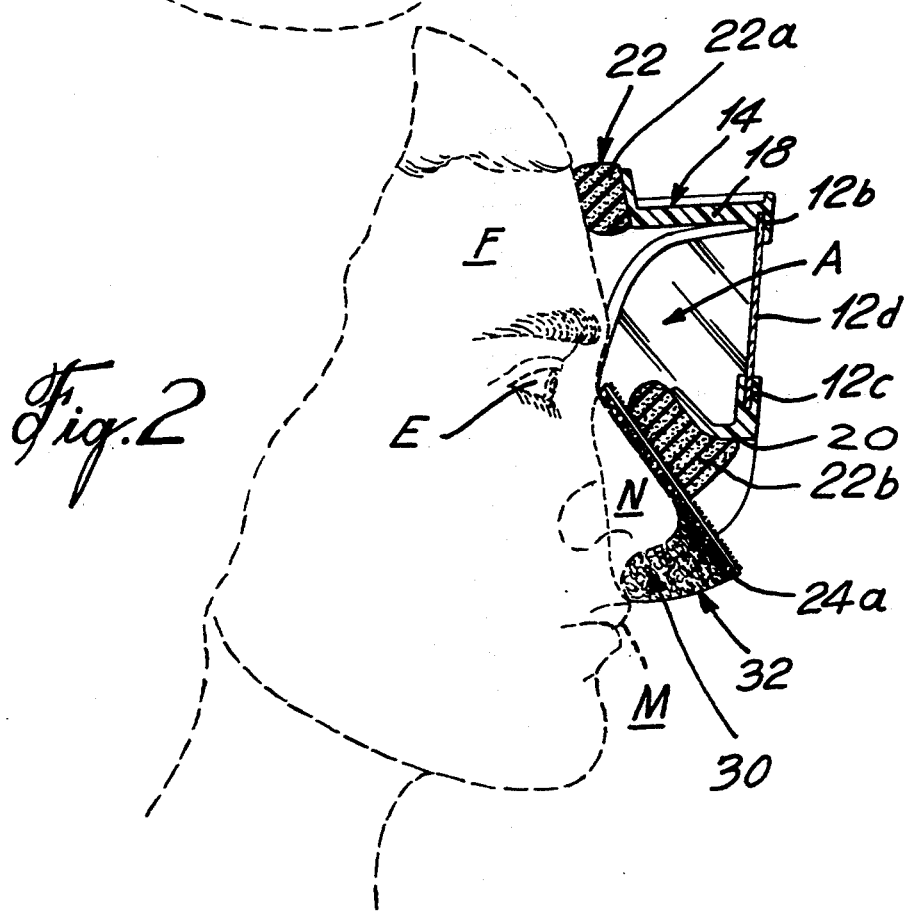

THERMAL NOSE PROTECTOR AND SKI GOGGLES

FIELD OF THE INVENTION

This invention relates to clothing for outdoor sports, particularly those for alpine skiers.

BACKGROUND OF THE INVENTION

Alpine ski is a popular outdoor sports activity in normally subfreezing (Celsius-wise) temperatures, whereby a skier wearing elongated skis at his feet descends at variable speeds over the snow-covered slope of a mountain. Upon reaching the valley, the skier can be brought to the mountain peak once again, through conventional power-operated conveying means. Such an up-and-down cycle may be repeated a number of times during a given day.

The power-operated skier conveying means can be generally subdivided into two distinct categories: first, the so-called T-bars, in which the skiers simply board successive open frame members linked to an endless drive cable and slide upwardly along the slope; and second, chair-lifts, teleferics and gondolas, which are supported in airborne fashion by an endless drive cable. The teleferic and the gondolas include closed cabins, through the door of which a few (for the gondola) or several (for the teleferic) skiers may enter and be transported thereinto. The teleferics and gondolas are clearly the most comfortable for the skiers, since they constitute a weatherproof self-enclosed bubble into which the skiers may warm up (through bodily heat convection between skiers) as they are conveyed to the mountain peak; but they entail large capital cost outlays, and this is why such costs can be recouped only in the largest ski centres where they are usually found (e.g. in the Mont Saint Anne ski resort near Québec City, for gondolas; or in the Jay Peak ski resort in Vermont, for teleferics). Another factor which would prevent otherwise important ski resort centres from investing into airborne cabin type powered ski lift apparatuses is the conditions where the average wind intensity is so high along the mountain slope as to create a swinging cabin condition preventing safe operation of an airborne cabin—this is the case for the otherwise major ski resort centre of Mont Tremblant in northern Québec.

Therefore, in most situations, not only does the skier sustain a thermal stress during descent, but also during ascent on the T-bar or chair-lift, the more so in the latter (ascent) case in that no heat-generating physical exercise is usually made during ascent, contrarily to the time of descent where the skier will use a large number of different body muscles to achieve a winding pathway along the slopes (as this physical activity per se is tied to his skiing enjoyment). Thus, ascent further contributes to the discomfort of the skier. Moreover, thermal stress does increase with altitude: temperature drops and winds gain speed; it is well known that high winds can substantially decrease the ambient temperature due to the so-called wind-chill factor (as effectively felt by a person's unprotected skin) which is well below the one effectively measured by Hg-based thermometers.

Hence, such compounding of environmental conditions (subfreezing temperature, increased weather harshness—including wind conditions—with increasing altitude, and decreased physical activity during powered ascent from valley to mountain peak) do constitute aggravating factors which compromise the comfort and thus the enjoyment of the skier. In extreme weather conditions, particularly where the temperature falls below the minus twenty degree Celsius mark and where the mountain peak is among the highest of the overall area, the period of time before which the limit threshold of thermal stress resistance is reached by the skier becomes very short, whereby the only remaining recourse for the skier is to undon his skis after each descent—or the like to—get into the heated ski chalet building for a warming period. This obviously reduces the enjoyment of the skier (not to speak of the cost-effectiveness of the purchase of his ski-lift pass), since his total effective skiing time for the given day is reduced.

Clearly, those areas which are first prone to suffer most from the cold are those of the skier's body which are not normally shielded by a thermally insulating fabric layer, i.e. usually the skier's face. Ski goggles can be used to protect part of the face skin exposed to the cold surroundings, but still, the nose and the cheeks usually remain exposed to frostbites. The cartilage-based nose is particularly at risk, because of the scarcity of fat therein and because it projects orthogonally from the face so that often, a nose becomes frostbitten so quickly that this goes unnoticed by the skier since, not feeling anything, he has no clue that such a situation has developed. Unthawing a nose can be a painful experience, or worse. Obviously, skiers may shield their nose with a wool scarf wound around their neck; but, since the scarf does hang ahead of the mouth and nose, it tends to impair breathing of the skier, particularly the heavy breathing associated with the type of skiing performed on the so-called expert (i.e. most challenging) slopes. Moreover, the wool scarf constitutes a screen against which will rebound the air breathed out from the nose, and this backflow of moist air will tend to cloud the otherwise transparent plastic pane of the ski goggles and or prescription glasses, thus compromising the vision—and thus the safety—of the skier.

OBJECTS OF THE INVENTION

Accordingly, it is the gist of the present invention to address the needs of snow skiers, by providing a thermal nose protector for decreasing the likelihood of nose frostbites.

A corollary object of the invention is to increase the level of comfort and enjoyment of snow skiers, particularly alpine skiers.

A further object of the thermal nose protector is to widen the range of outdoor temperatures within which an alpine skier will be able to ski comfortably for a given length of time.

An object of the invention is that the thermal nose protector include means for alerting the skier of the beginning of a cheek frost-bite condition.

Another object of the thermal nose protector is to effectively reduce the likelihood of nose frostbite, while not impairing breathing of the skier, even when breathing is heavy.

An object of the thermal nose protector is to prevent the clouding over of ski goggles or prescription glasses from the breathing out of the skier.

A further object of the invention is to provide a thermally insulating nosepiece, which will be of very low manufacturing cost, while being adaptable to substantially all commercially available ski goggles.

SUMMARY OF THE INVENTION

Accordingly with the objects of the invention, there is disclosed a thermal nose protector for use by a person in subfreezing climates, said thermal nose protector including: (a) at least a first and a second flexible sheet layers, at least said first sheet layer being sized to conformingly fit over and directly engage the contour of a person's nose, said second sheet layer being of an airtight nature and extending along at least a substantial surface area of said first sheet; (b) means for bonding said sheet layers to one another in superimposed fashion; and (c) means for supporting said sheet layers over the person's nose and for maintaining same thereagainst; wherein at least said second sheet layer extends beyond the tip of the person's nose whereby a substantially open air chamber is defined within the area circumscribed by the second sheet layer beneath the nose tip and ahead of that person's mouth, wherein an air breathing channel is formed coextensively of said open air chamber for promoting air breathing from the nose in an environment shielded from a frontwardly-incoming icy wind. Preferably, the securing means is of the hook and loop fastening type.

This invention also relates to a thermal nose protector for use with ski goggles by a skier in subfreezing temperatures, said ski goggles of the type having a unitary transparent pane supported by an integral frame to extend in a curved plane in the path of the wearer's field of vision, said ski goggles frame having an interior edge with a foam-like strip engaging the skier's face (including the contour of the nose) whereby a substantially closed air chamber is formed; said thermal nose protector consisting of a flexible shield sheet material sized to conformingly fit over the skier's nose and having at least a first and a second layer, said first layer made from a soft material for direct engagement with the skin of said skier's nose, said second layer of the multiple-hook type for separable gripping engagement with a corresponding portion of said foam-like strip of the ski goggles, said flexible shield sheet extending beyond the tip of said skier's nose whereby a substantially open air chamber is defined by the nose-covering said shield sheet beneath the skier's nose and ahead of the skier's mouth, wherein an air breathing channel is formed coextensively to said open air chamber for promoting air breathing from the nose of the skier, said air breathing channel extending generally transversely of the direction of displacement of the skier whereby the nose of the skier is thermally protected from incoming wind.

Preferably, at least one of said sheet layers has at least some thermally insulating properties. Moreover, said shield sheet could be composed of the back to back combination of a pair of hook and look type fastener members.

Advantageously, said hook and loop type shield sheet is selected from the group of such sheets disclosed in Canadian patent application No. 1,279,978 laid open on 12 Feb. 1991.

Said first and second sheet layers could be permanently anchored to one another. Or, alternately, a third flexible sheet layer could be added, being sandwiched between said first and second layers, at least one of said first and second sheet layers being separable from said sheet layer and replaceable by a fresh layer when the useful lifetime of the former has expired.

The invention also relates to permanently anchoring two layers of material to one another, the first layer made of a soft material to engage the nose and the second, made from a flexible VINYL like material on which a strip of hook fastening is permanently bonded to allow the nose protector to be attached to the foam like material around the perimeter of the ski goggle.

BRIEF DESCRIPTION OF THE DRAWINGS

FIG. 1 is an isometric view of a person's head, in phantom lines, with ski goggles fitted therearound and to which is secured the thermal nose protector of the invention;

FIG. 2 is a side elevation of the elements of FIG. 1, but showing the ski goggles and thermal nose protector in cross-section;

DETAILED DESCRIPTION OF THE DRAWINGS

Figure 3:
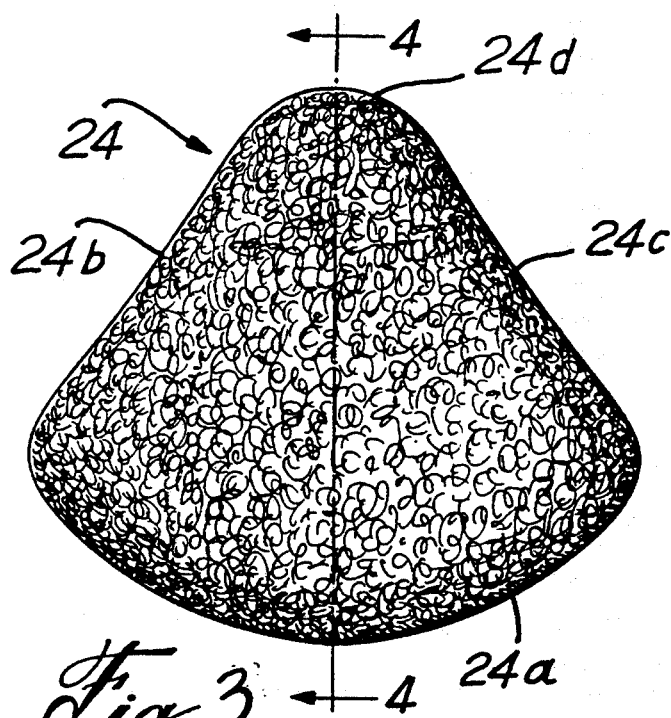
FIG. 3 is a plan view of the thermal nose protector.

The head H of a person P is illustrated in FIGS. 1 and 2, and defines inter alia a forehead F, eyes E, a nose N, cheeks C and a mouth M. Ski goggles 10, not forming part of the invention as such, are releasably installed to the head of person P. Ski goggles 10 defines a unitary transparent pane, 12, located to extend in a curved plane in the path of the wearer's field of vision, both frontally and sidewisely thereof. Elongated pane 12 includes an intermediate notch 12a, for accommodating i.e. clearing the nose N. A semi-rigid plastic frame 14 is provided, for supporting pane 12 ahead of the eyes E. An elastic strap 16 releasably tightly connects frame 14 and associated pane 12 to head H. Frame 14 thicknesswisely tapers downwardly to define a relatively wider upper section 18 and a comparatively narrower lower section 20. The foremost edge portion of frame 14, including sections 18 and 20, carry the peripheral edge of the panes, including top and bottom edge portions 12b and 12c, respectively, whereby the transparent pane is mounted at a fixed location spacedly ahead of the eyes E. The interior edge portion of the whole frame 14 engages the skin of person P via an integral foam band 22, i.e. along contacting portions of the forehead F (foam band section 22a), cheek C and nose N (foam band section 22b), whereby a substantially closed, weatherproof air chamber A is defined by the volume formed by pane 12, frame 14, and the thus enclosed registering epiderm of the face part of head H. Nose N does not engage into the closed air chamber A, but escapes outwardly therefrom through the notch 12a. Nose N usually extends short of a plane tangent to the registering section 12d (FIG. 2) of the pane 12.

FIGS. 3, 4—4a and 5 show the thermal nose protector 24 of the present invention. Thermal nose protector 24 is formed of a flat, flexible sheet defining two (FIG. 4) or three (FIG. 4a) sheet layers. As illustrated in FIG. 3, nose protector 24 is sized to conformingly fit over the nose N, whereby a roughly triangular shape is achieved in plan view (or V-shape in operative condition in cross-sectional view) except that one side edge 24a thereof forms a wide convex "belly". The two other side edges will be referenced 24b and 24c, and these latter side edges merge at apex 24d opposite side edge 24a.

Figure 4:
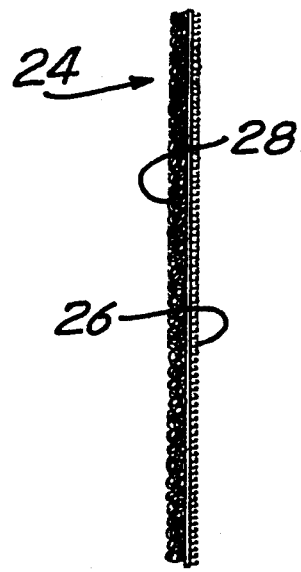
FIGS. 4 and 4a are cross-sectional views along lines 4—4 of FIG. 3, illustrating two alternate embodiments of thermal nose protector.

In the first embodiment of nose protector 24 illustrated in the edgewise view of FIG. 4, the first layer consists of a multiple hook type fastener member 26, while the second layer on the face opposite first layer 26 consists of a smooth piled member 28, layers 26 and 28 being permanently interconnected e.g. by a suitable glue compound. Preferably, piled member 28 is of the multiple loop fastener member type (e.g. of adjustable density), whereby sheet 26, 28, would be made from strips of the so-called hook-and-loop fastener members.

Hook and loop fasteners have been known for quite some time, and many different types of materials and fabrics have been adapted for coaction therewith to effect joining of associated structures. Applications are found in the wearing apparel, for recreational equipment, covers for cars and boats, and the like. Basically, these known hook and loop fastening bands are usually made from any moldable plastic material, nylon or polypropylene, with the hook-type engaging element being constructed from a monofilament loop, one leg of which is either cut or removed to transform the loop into a hook. However, mushroom-type hook members are not to be considered as excluded from the scope of the present invention, and should be considered to be encompassed within the scope of definition of the hook member. The main differences between hook-type fasteners and mushroom type fasteners can be summarized as follows:

- with the hook surface, the forces required to peel the hook loop separable members is usually lower than the forces required to peel the mushroom-loop separable members;
- the shear force required to separate the members along the interfacial plane of engagement is much greater with mushroom fasteners than with hook fasteners; and
- the useful, i.e. operational, life cycle for mushroom-loop fasteners is much lower than for hook-loop fasteners.

Thus, the piled layer 28 may be soft, loop-type elements such as those used in known hook and loop fasteners; this is cost-effective—such hook and loop elements are currently available on the market. However, it should be understood that the present joint inventors do not wish to be limited thereto, and any other type of suitably soft, thermally insulating fabric material, not excluding foam and the like, could be envisioned to replace the multiple loop element.

In the present invention, the multiple hook element 26 of a first sheet 24 is not to engage with the multiple loop element 28 of a second sheet 24, as in conventional hook and loop fastening joints. On the contrary, and as suggested in FIG. 2 of the drawings, in the operative position of the thermal sheet 24, at least a fraction of the total surface of the multiple loop (or piled) element 28 is to directly engage the skin of the nose N of the person's face, with sheet apex 24d reaching the section of nose N located between the person's two eyes E, E, while the opposite "belly" side edge 24a of sheet 24 will extend beyond nose N and away from the person's face. Preferably, edge 24a extends approximately in vertical register with pane section 12d. Preferably also, lower sheet edge 24 generally clears mouth M, i.e. extends within a horizontal plane located above mouth M (when eyes E look to the horizon, as suggested in FIG. 2).

As suggested in FIG. 1, the thermal sheet 24, in its operative nose-covering position, does disclose an aerodynamic contour which tends to desirably deflect incoming air laterally outwardly of the nose.

Thermal sheet 24 is releasably maintained in its said operative condition by the releasable interlocking engagement of the multiple hook face 26 of the sheet 24 with the lower section 22b of the foam strip 22 which integrally extends along the interior edge of the ski goggles frame 14. It has been found by the joint inventors that most if not all of the commercially available ski goggles 12 had foam or foam-like interior strips, 22, which were functionally similar i.e. equivalent to the piled or multiple loop member from hook-and-loop fastening assemblies. The hooks on the sheet face 26 do effectively grip the "loops" formed by the air cells of the foam backing 22, firmly but in a separable fashion, in the same way as for hook-and-loop fastening assemblies. As for the piled or loop face 28 of thermal sheet 24, it has no securing purpose, only a thermally insulating purpose and a comfort-enhancing surface for engagement with the skin.

It can now be readily understood from FIG. 2 that a wind-shielded, substantially open air chamber 30 is defined by the foremost part of thermal sheet 24, i.e. at a location beneath nose N and ahead of mouth M, up to the wide, convex, freely overhanging sheet edge or mouth 24a of the nosepiece 24. Due to the roughly triangular shape (in plan view) of nosepiece sheet 24, a half funnel-shape member is formed when the nosepiece is bent in its operative condition conformingly against the nose N, to form a generally V-shape in cross-section as illustrated, with the diametrally larger end mouth 24a of the funnel shape member 24 being located on the side generally opposite the person's face. Thus, an air breathing channel, 32, can be said to be concurrently formed by the nose covering nosepiece 24, for facilitating breathing through nose N. Those skilled in the art of alpine ski will readily appreciate that a skier, during his descent mode, does shift his centre of gravity forwardly for enhanced directional control of his skis, whereby the head will necessarily move forward and downward; this therefore brings the conical air breathing channel 32 along a downwardly oriented, substantially vertical axis, thus substantially preventing incoming air from engaging into the open pocket 30 of the speeding skier and thus reducing the likelihood of nose or mouth frostbites due to the wind-chill factor.

Another advantageous feature of the present thermally insulating nose piece is that the sheet edges 24b and 24c, by transversely engaging parts of the cheeks C, will chaff same periodically as the head H shakes from periodic ground impact blows of the skier's skis, during skier's descent. This is advantageous, in that this chaffing will constitute a clue to allow the skier's to identify the beginning of a skin freezing condition about the cheek portion of his face. Frostbites will therefore be less likely about the cheeks.

Figure 4A:
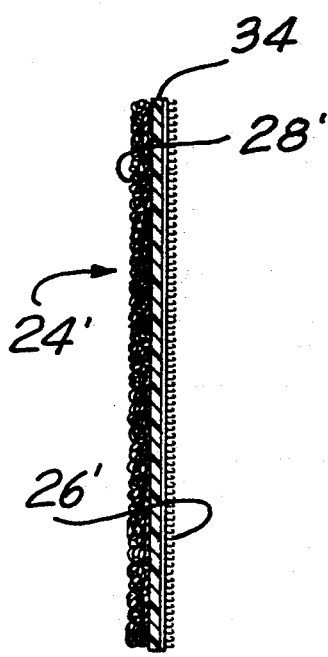
Figure 5:
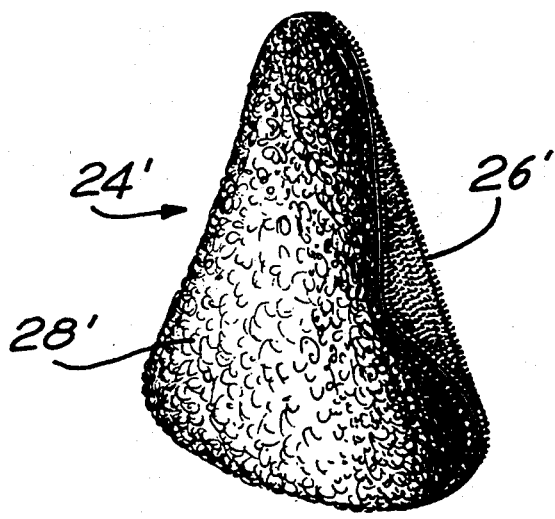
FIG. 5 is an isometric view of the nose protector embodiment of FIG. 5, being shown in a partially peeled off condition.

In the alternate embodiment of thermal sheet illustrated as 24' in FIG. 4a, there is sandwiched between the piled layer 28' and the hook layer 26' a flexible template layer, 34. Flexible template layer 34 could be made for example from a plastic material, preferably vinyl In thermal sheet 24', at least one layer 26' or 28' is separable from the intermediate vinyl backing 34, as generally suggested in FIG. 5 of the drawings. Such a separable sheet layer 26' or 28', particularly the multiple-hook sheet layer 26', can then be replaced by a fresh one, when the useful life cycle of the former has expired.

It is understood that, whenever use of the nosepiece 24 is not required, it can be easily removed from goggles 10 simply by detaching the thermal nosepiece hook face 26 from the foam strip 22b of the ski goggles. Its use is very simple for the consumer. Since the nosepiece 24 is made only from flexible sheet material, it takes minimal storage space when not in use; and since it is preferably manufactured from readily available, very low cost hook and loop fastener rolls, it is of very low manufacturing cost.

In extremely cold weather conditions, it may be required to add one or a few additional thermal sheets 24, 24, superimposed over one another, with the multi-hook face of one sheet 24 lockingly engaging the multi-loop face of the following sheet 24, to increase the thermal insulation. The nosepiece 24, made from such a combination of superimposed sheets 24, 24, . . . , would still remain fully operational, albeit less flexible because of the increased thickness thereof), since the resultant nose piece would still present a free multi-hook first face and an opposite free multi-loop second face.

The multiple-hook layer 26 could be made of an extruded, woven or knitted construction, and manufactured initially from a sheet of any width or length. The sheet member would then be cut and shaped for adherence to the flexible template member 34.

I claim:

1. In combination, a thermal nose protector and ski goggles to which the thermal nose protector is releasably attached in an operative position thereof, said ski goggles having a unitary transparent pane supported by an integral frame to extend in a curved plane in the path of the wearer's field of vision, said ski goggles frame having a peripheral interior edge carrying a foam-like strip, having air pockets, said strip engaging the skier's face whereby a substantially closed air chamber is formed ahead of the skier's face within said ski goggles, said interior edge pile strip defining a lower intermediate portion adapted to extend transversely over a fraction of the wearer's nose; said thermal nose protector consisting of:
   (a) first flexible sheet, sized to conformingly fit over all of the skier's nose, said first sheet made from a soft thermally insulating sheet material, said first sheet adapted for direct engagement with the skin of said skier's nose;
   (b) a second flexible sheet defining a main portion with an external surface made from a multi-hook, airtight sheet material, said hooks complementary to the air pockets formed on the foam-like strip of said ski goggle lower intermediate portion, said second sheet having inner and outer edge portions, said second sheet main portion flatly engaging in operative position against said, air pockets of said lower intermediate portion of said ski goggles, said second sheet inner edge portion extending in operative position inwardly beyond said foam-like strip of said lower intermediate portion of ski goggles and into said ski goggles closed air chamber, the multiple hooks of said second sheet main portion releasably gripping the said complementary air pockets of said lower intermediate portion of said foam-like strip of the ski goggles in hook and loop fastening fashion, whereby the thermal nose protector is adapted to become sandwiches between the wearer's nose and the lower intermediate portion of the ski goggles, said second airtight sheet outer edge portion also sized to extend in operative position beyond the tip of said skier's nose whereby a substantially open air chamber is defined by the thermal nose protector outer edge portion beneath the skier's nose and ahead of the skier's mouth; and
   (c) bonding means, fixedly interconnecting said first and second sheets flatly against one another; wherein an air breathing channel is formed coextensively of said open air chamber for promoting air breathing from the nose of the skier, said air breathing channel to extend generally transversely of the direction of displacement of the skier whereby the nose of the skier is to be shielded from incoming cold air.

2. Ski goggles as defined in claim 1, wherein said first and second flexible sheets are of the same size and edgewisely match each another.

3. Ski goggles as defined in claim 2, wherein said thermal nose protector is of generally triangular shape, except that one of the three edges thereof forms a pronounced convex edge, said convex edge forming a free outer edge defined by said outer edge portion of the thermal nose protector.

* * * * *